United States Patent
Taub et al.

(10) Patent No.: US 8,944,068 B2
(45) Date of Patent: Feb. 3, 2015

(54) DRAPE

(76) Inventors: Stanley Taub, New York, NY (US);
Thomas Butsch, Tuttlingen (DE)

( * ) Notice: Subject to any disclaimer, the term of this patent is extended or adjusted under 35 U.S.C. 154(b) by 166 days.

(21) Appl. No.: 13/574,713

(22) PCT Filed: Jan. 25, 2011

(86) PCT No.: PCT/US2011/022373
§ 371 (c)(1),
(2), (4) Date: Sep. 18, 2012

(87) PCT Pub. No.: WO2011/091406
PCT Pub. Date: Jul. 28, 2011

(65) Prior Publication Data
US 2013/0056011 A1    Mar. 7, 2013

Related U.S. Application Data

(60) Provisional application No. 61/297,922, filed on Jan. 25, 2010.

(51) Int. Cl.
*A61F 5/37* (2006.01)

(52) U.S. Cl.
USPC .......................................... 128/849; 128/852

(58) Field of Classification Search
USPC .................... 128/849–856; 493/243
See application file for complete search history.

(56) References Cited

U.S. PATENT DOCUMENTS

| | | |
|---|---|---|
| 5,010,899 A | 4/1991 | Thompson |
| 5,059,271 A | 10/1991 | Taub |
| 5,339,831 A | 8/1994 | Thompson |
| 6,213,124 B1 | 4/2001 | Butterworth |
| 6,314,959 B1 | 11/2001 | Griesbach et al. |
| 6,615,836 B1 * | 9/2003 | Griesbach et al. ............ 128/849 |
| 6,874,505 B1 * | 4/2005 | Fenwick et al. ............ 128/849 |

* cited by examiner

*Primary Examiner* — Michael A. Brown
(74) *Attorney, Agent, or Firm* — Lucas & Mercanti, LLP

(57) ABSTRACT

A pouch formed from sheet material that is commonly referred to as a drape. The pouch is formed by folding the drape, which has a tacky surface, on itself and placing fasteners through holes punched in the drape which ensures the pouch maintains is maintained. The pouch catches medical instruments that may slide off of the drape, preventing the medical instruments from failing to the floor and becoming contaminated.

10 Claims, 4 Drawing Sheets

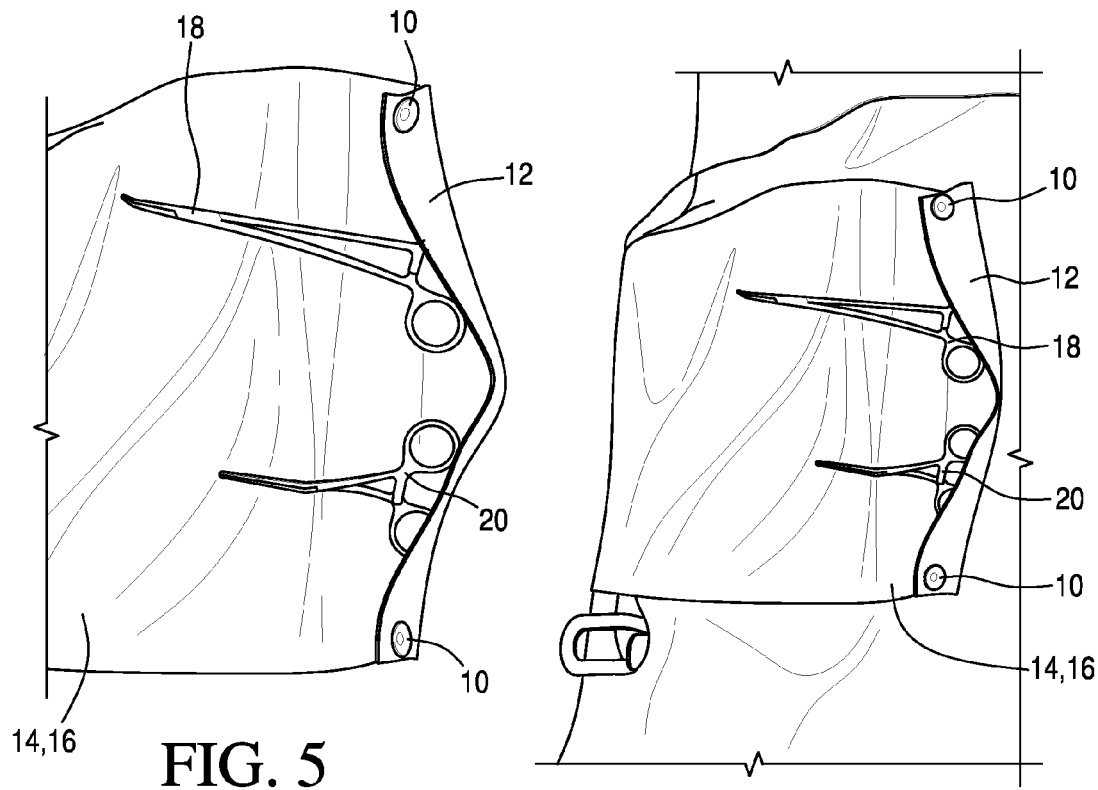
FIG. 5
FIG. 6
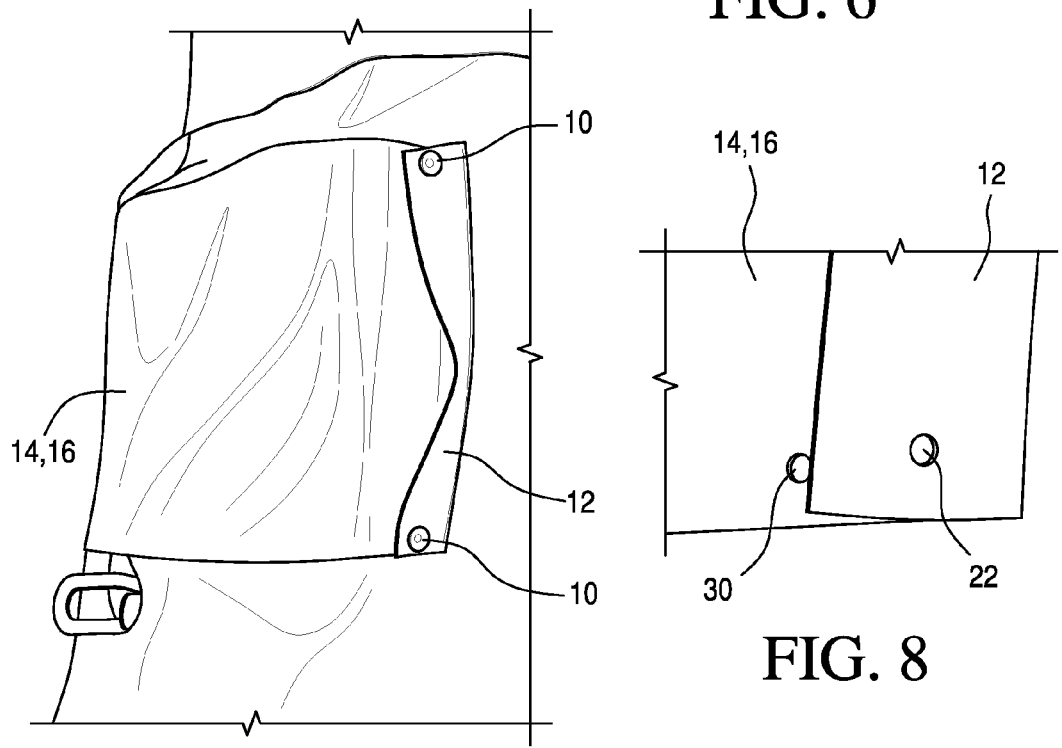
FIG. 7
FIG. 8

DRAPE

CROSS-REFERENCE TO RELATED APPLICATIONS

This application is a 371 of PCT/US2011/022373 filed Jan. 25, 2011, which in turn claims the priority of U.S. 61/297,922 filed Jan. 25, 2010, the priority of both applications is hereby claimed and both applications are incorporated by reference herein.

FIELD OF INVENTION

The present invention relates to drape with a pouch used during medical procedures.

BACKGROUND OF THE INVENTION

In an operating room, a patient is usually placed in a supine position and then covered with sterile paper drapes. However, there is a 90% chance that surgical instruments placed on these sloping paper drapes will slide off to the floor. This slippage problem causes delays with surgery because of the need to re-sterilize the contaminated instruments. In the 1960's to reduce the frequency of falling instruments, magnetic reusable instrument holding drapes were developed. These magnetic drapes, while still in use, have drawbacks. They magnetize instruments and interfere with pacemakers. Further, magnetic drapes cannot hold plastic instruments on sloping surfaces and they have irregular lumpy surfaces which hold magnets that add to its weight and inflexibility.

A method of supporting and retaining surgical instruments on a non-skid supporting surface was patented in 1991, see U.S. Pat. No. 5,059,271. The non-skid drape of U.S. Pat. No. 5,059,271, which is commonly referred to under the trademark Insta-Hold™, eliminated the need for magnets as the drape's light tackiness is capable of holding surgical instruments both metal and plastic on any sloping surface and is completely flexible and light weight. However, in spite of these improvements, sterile surgical instruments can slip from the tacky surface of the drape and fall to the floor.

SUMMARY OF THE INVENTION

The present invention relates to a pouch formed from sheet material commonly referred to as a drape. The pouch is formed by folding the drape, which has a tacky surface, on itself and placing fasteners through holes punched in the drape which ensures the pouch maintains is maintained. The pouch catches medical instruments that may slide off of the drape, preventing the medical instruments from falling to the floor and becoming contaminated.

Broadly, the present invention can be defined as a drape having a pouch, which comprises long sides, short sides perpendicular to the long sides, outer holes located just proximal to the long sides of the drape, inner holes located inward of the outer holes, closer to a center of the drape, and fasteners which are placed through the outer holes and the inner holes, forming the pouch.

The fasteners can be, for example, sterile grommets. The drape can be nineteen inches by twelve inches. Alternatively, the drape can be nineteen inches by twenty-four inches. The inner holes and the outer holes can be one-eighth inch in diameter.

The long sides of the drape are folded inward, toward the center of the drape a distance of approximately three inches to form the pouch. The pouch has a depth of approximately four inches.

Further holes can be present inward and parallel to the outer holes.

Also, the present invention can be defined as a method of forming a pouch, which comprises the following steps: creating the inner holes and the outer holes in the drape; folding each outer edge of the drape inward, toward a center of the drape; placing the fastener through the outer holes; and placing the fastener through the inner holes.

BRIEF DESCRIPTION OF THE DRAWINGS

The present invention will be further understood and appreciated by reading the following description in conjunction with the accompanying drawings, in which:

FIG. 5 is a sectional view of the pouch of the present invention;

FIG. 6 is a sectional view of the pouch of the present invention;

FIG. 7 is a sectional view of the pouch of the present invention;

FIG. 8 is a sectional view of the pouch of the present invention;

DETAILED DESCRIPTION OF THE INVENTION

Figure 1:
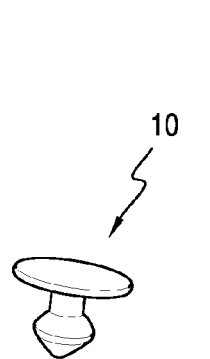
FIG. 1 is a perspective view of a fastener of the present invention.

Referring now to the drawings, in which like reference numerals refer to like reference parts throughout, FIG. 1 shows a sterile fastener 10 which aids in forming pouches 12 from sheet material 14, which is commonly referred to as a drape. Preferably, a sterile faster 10 is a grommet. However, any known suitable fastener could also be used. The drape 14 has a top, smooth tacky surface 16 and a bottom, rough textured surface (not shown). The textured surface acts to hold the drape 14 in place.

Typically, the drape 14 is placed over a patient who is being operated on. The doctor may then place surgical instruments on the drape 14. These instruments may include metallic and non-metallic instruments, such as scissors 18 and 20 or other instruments not known, including a scalpel, clamps, scissors, plastic suction tubes and plastic pens. In light of the tacky surface 16, surgical instruments can lose their footing and slide off of the drape 14. However, the pouches 12 aid in preventing any medical instrument that may become dislodged from falling to the ground and requiring re-sterilization.

Figure 2:
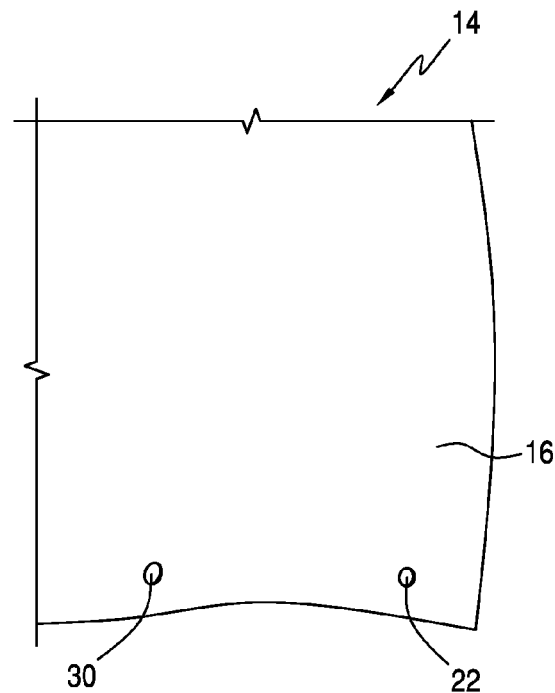
FIG. 2 is a sectional view of the drape of the present invention.
Figure 3:
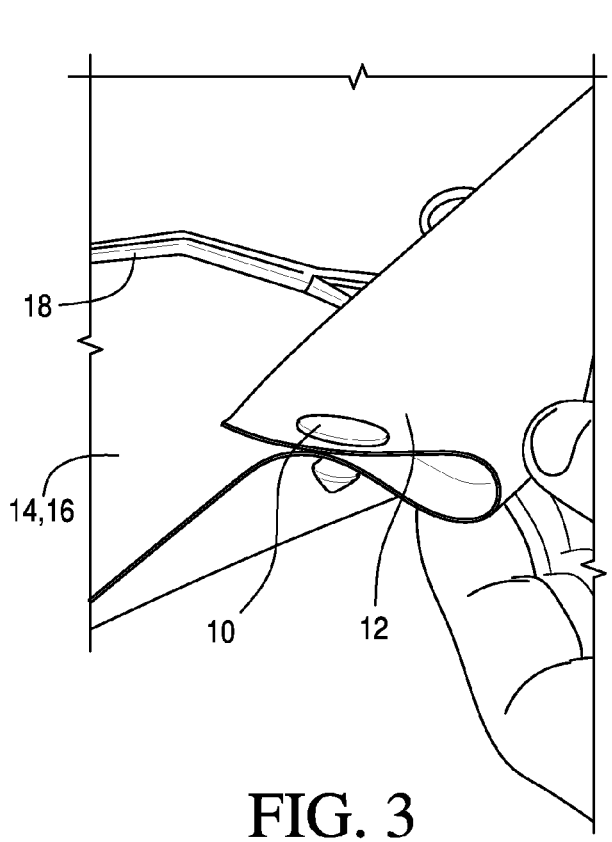
FIG. 3 is a sectional view of the pouch of the present invention.
Figure 4:
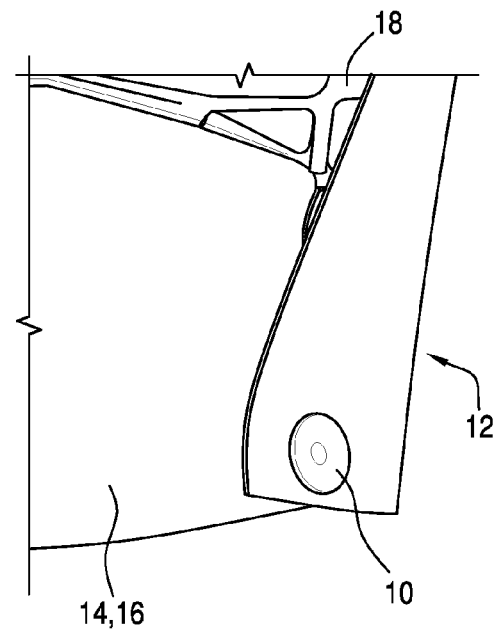
FIG. 4 is a sectional view of the pouch of the present invention.

FIG. 2 is a sectional view that shows a drape 14 prior to the formation of the pouch 12. The drape 14 has outer holes 22, 24 which are approximately one-eighth inch in diameter that are located just proximal to the edges of the long sides 26, 28 of the drape 14 and inner holes 30 which are approximately spaced four inches along the short sides 32, 34 inward from the outer holes 22, 24, toward the center of the drape 14. However, the holes 22, 24, 30 can be of any suitable diameter and the spacing between the inner holes 30 and outer holes 22, 24 can be greater or less than four inches.

FIG. 3-7 show the pouch 12 which is used to ensure surgical instruments do not fall off of the drape 14 and onto the floor. As can be seen, the pouch 12 is formed by placing the fastener 10 through the outer holes 22, 24, folding the corners of long side 26, 28 of the drape 14 approximately three inches on itself, as can be seen in FIG. 8, and then pushing the fastener 10 through the inner holes 30. Each pouch 12 is thus approximately four inches deep. Instruments losing their footing on the tacky surface of the drape 14 will fall into the pouches 12 for easy and non-contaminated retrieval.

Figure 9:
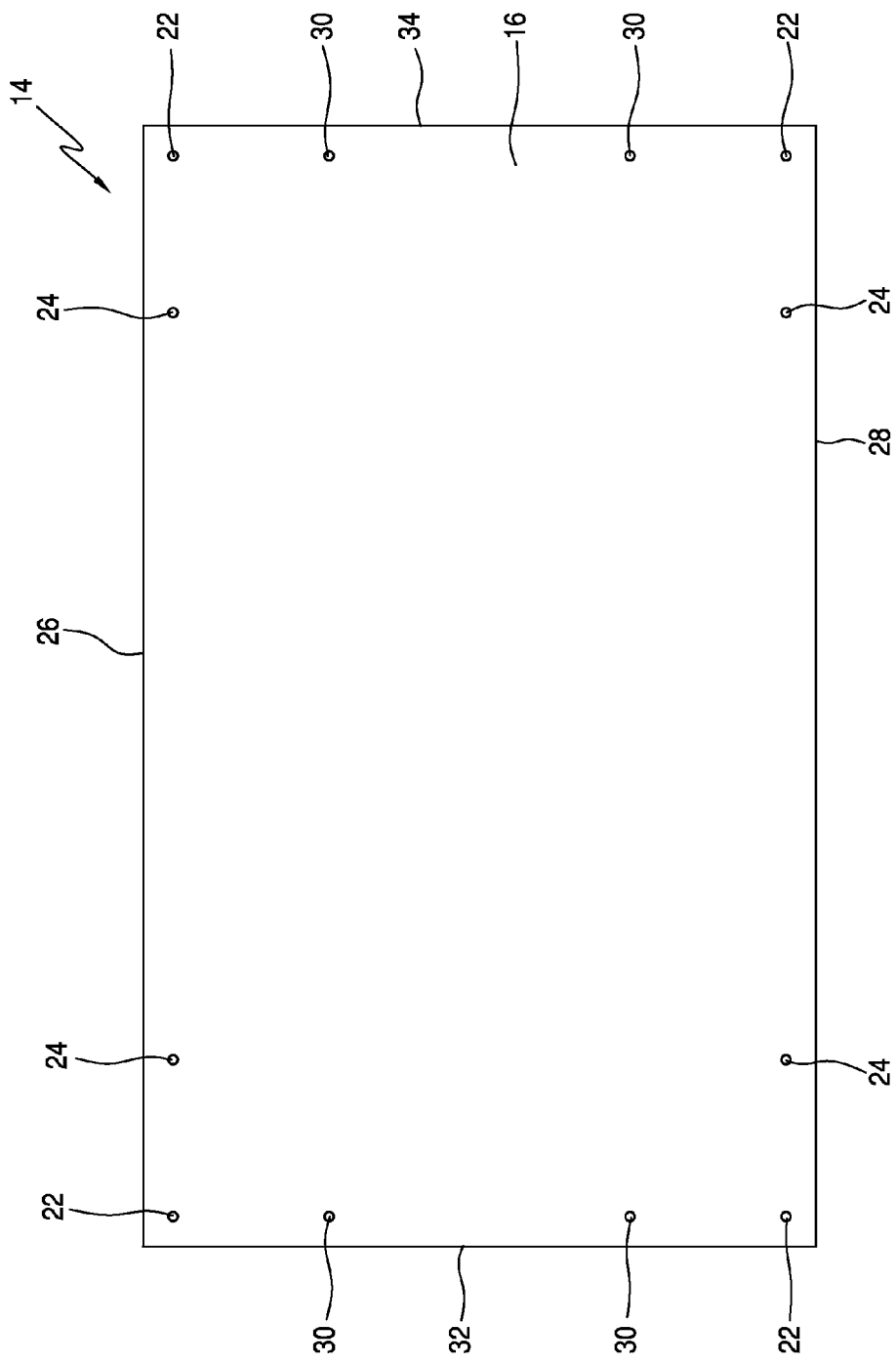
FIG. 9 is plan view of the drape.
Figure 10:
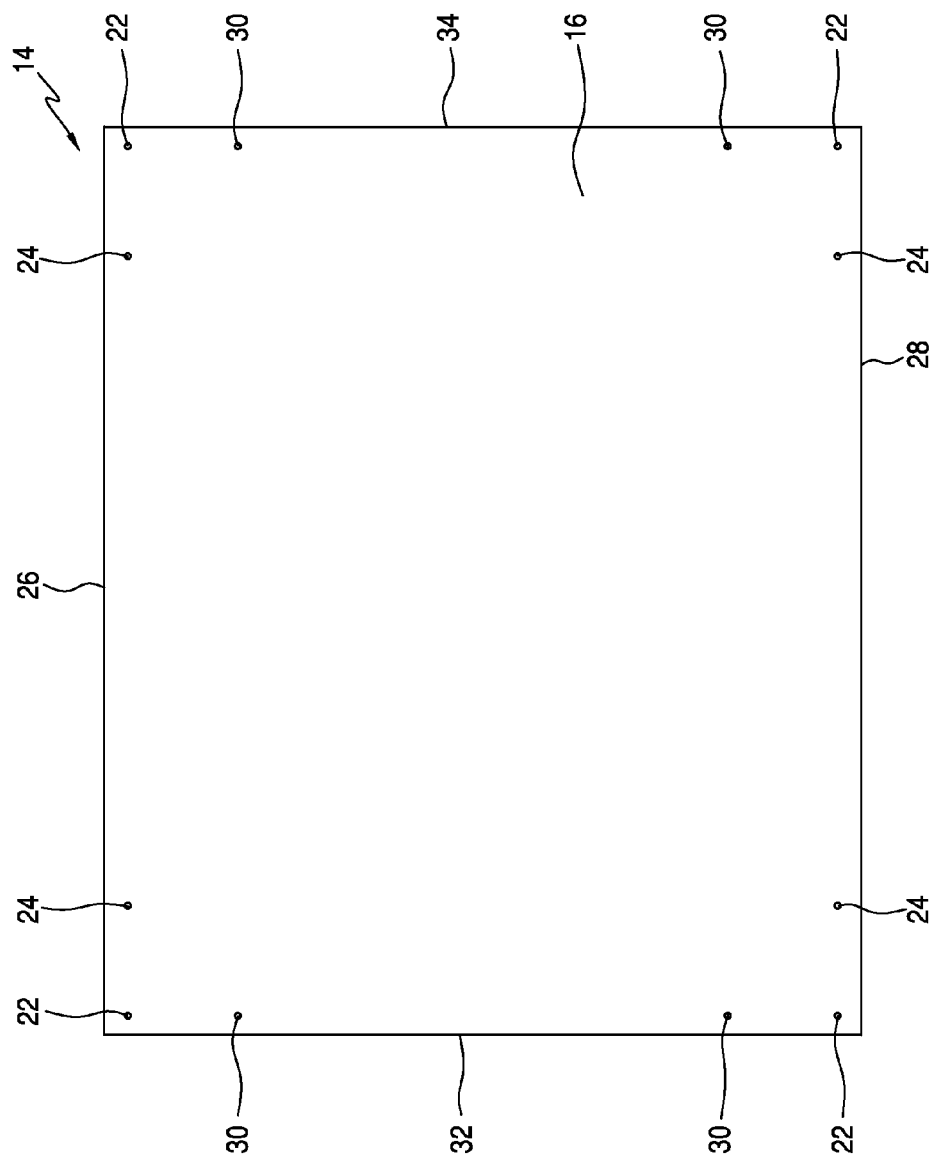
FIG. 10 is a further plan view of the drape.

FIGS. 9-10 show the drape 14 and holes 22, 24, 30 prior to formation of the pouches 12. The drape 14 can be of any suitable size. However, It is preferred that the drape 14 is roughly nineteen inches by twelve inches or nineteen inches by twenty-four inches.

The present invention has been described with reference to a preferred embodiment. It should be understood that the scope of the present invention is defined by the claims and is not intended to be limited to the specific embodiment disclosed herein.

What is claimed:

1. A drape having a pouch, comprising:
    first sides;
    second sides substantially perpendicular to the first sides;
    outer holes located proximate the first sides;
    inner holes located inward of the outer holes, closer than the outer holes to a center of the drape; and
    fasteners which are placed through the outer holes and the inner holes, forming a pouch.

2. The drape of claim 1, wherein the fasteners are sterile grommets.

3. The drape of claim wherein the drape is nineteen inches by twelve inches.

4. The drape of claim 1, wherein the drape is nineteen inches by twenty-four inches.

5. The drape of claim 1, wherein the inner holes and the outer holes are one-eighth inch in diameter.

6. The drape of claim 1, wherein the first sides of the drape are folded inward, toward the center of the drape a distance of approximately three inches.

7. The drape of claim 1, wherein the pouch has a depth of approximately four inches.

8. The drape of claim 1, wherein further holes are present inward and parallel to the outer holes.

9. A method of forming a pouch of claim 1, comprising the following steps:
    creating the inner holes and the outer holes in the drape;
    folding each outer edge of the drape inward, toward the center of the drape;
    placing the fastener through the outer holes; and
    placing the fastener through the inner holes.

10. A drape system for use during medical procedures, the drape system comprising:
    a drape comprising:
        first, second, third, and fourth edges forming a substantially rectangular shape, wherein the first edge is opposite the second edge;
        two first pairs of holes associated with the first edge, each first pair of holes including a first outer hole located proximate the first edge and a corresponding first inner hole located approximately tour inches inward from the first outer hole;
        two second pairs of holes associated with the second edge, each second pair of holes including a second outer hole located proximate the second edge and a corresponding second inner hole located approximately four inches inward from the second outer hole; and
    a plurality of fasteners;
    wherein the drape is adapted to be manipulated to form two pouches by:
        placing a respective fastener through the first outer hole and through the first inner hole of each respective first pair of holes to form a first pouch associated with the first edge; and
        placing a respective fastener through the second outer hole and through the second inner hole of each respective second pair of holes to form a second pouch associated with the second edge.

* * * * *